United States Patent
Ory et al.

(10) Patent No.: US 6,692,506 B1
(45) Date of Patent: Feb. 17, 2004

(54) ABSORBABLE PROSTHETIC MOUNTING CLIP

(75) Inventors: Francois Regis Ory, Fontaines Saint Martin (FR); Michel Therin, Lyons (FR); Jacqueline Huet-Olivier, Saint Ismier (FR)

(73) Assignees: Sofradim Production, Villefanche sur Saone (FR); Phusis, Saint Ismier (FR)

( * ) Notice: Subject to any disclaimer, the term of this patent is extended or adjusted under 35 U.S.C. 154(b) by 0 days.

(21) Appl. No.: 09/601,407
(22) PCT Filed: Feb. 3, 1999
(86) PCT No.: PCT/IB99/00190
§ 371 (c)(1), (2), (4) Date: Oct. 19, 2000
(87) PCT Pub. No.: WO99/39645
PCT Pub. Date: Aug. 12, 1999

(30) Foreign Application Priority Data

Feb. 3, 1998 (FR) .............................. 98 01509

(51) Int. Cl.$^7$ .............................. A61B 17/08
(52) U.S. Cl. .................. 606/151; 606/144; 606/221
(58) Field of Search ........................ 606/151, 152, 606/153, 154, 155, 144, 139, 232, 221

(56) References Cited

U.S. PATENT DOCUMENTS

| | | | |
|---|---|---|---|
| 3,399,432 A | | 9/1968 | Merser |
| 3,716,058 A | | 2/1973 | Tanner, Jr. |
| 3,875,648 A | * | 4/1975 | Bone .................. 606/221 |
| 3,995,581 A | | 12/1976 | Smejda |
| 4,006,747 A | | 2/1977 | Kronenthal et al. |
| 4,111,347 A | | 9/1978 | Bone |
| 4,121,487 A | | 10/1978 | Bone |
| 4,235,238 A | | 11/1980 | Ogiu et al. |
| 4,657,461 A | | 4/1987 | Smith |
| 4,669,473 A | | 6/1987 | Richards et al. |
| 4,696,300 A | | 9/1987 | Anderson |
| 4,705,040 A | | 11/1987 | Mueller et al. |
| 4,736,746 A | | 4/1988 | Anderson |
| 4,741,330 A | | 5/1988 | Hayhurst |
| 4,744,364 A | | 5/1988 | Kensey |
| 5,053,046 A | | 10/1991 | Janese |
| 5,203,864 A | | 4/1993 | Phillips |
| 5,290,296 A | | 3/1994 | Phillips |
| 5,320,633 A | | 6/1994 | Allen et al. |
| RE34,857 E | | 2/1995 | Kunreuther |
| 5,470,337 A | * | 11/1995 | Moss .................. 606/139 |
| 5,601,571 A | | 2/1997 | Moss |
| 5,755,371 A | | 5/1998 | Huang |
| 5,810,848 A | | 9/1998 | Hayhurst |

(List continued on next page.)

FOREIGN PATENT DOCUMENTS

| | | |
|---|---|---|
| WO | WO 87/01270 | 3/1987 |
| WO | WO 98/51179 | 11/1998 |

*Primary Examiner*—Julian W. Woo
(74) *Attorney, Agent, or Firm*—Oliff & Berridge, PLC

(57) ABSTRACT

The invention concerns a prosthetic mounting clip (1) having a monolithic structure, made of a biologically absorbable plastic material, comprising a distal anchoring element (2) in an anatomical support (8), a proximal stop element (3) relative to a prosthetic part (9), and a connecting rod (4) linking the distal anchoring element (2) and the proximal stop element (3), the connecting rod (4) being arranged relative to the distal anchoring element (2), to determine at least two positions of said connecting rod (4), namely an inoperative position wherein the connecting rod (4) is arranged along a direction (R) relative to the distal anchoring element (2), and another stressed position wherein the connecting rod (4) is folded back against the distal anchoring element (2) along a second direction (P). The invention is characterised in that, in the inoperative position of the connecting rod (4), the first direction (R) is inclined relative to the second direction (P), parallel to the anchoring element (2), at an acute angle not greater than 90°, and for example equal to about 45°.

7 Claims, 1 Drawing Sheet

U.S. PATENT DOCUMENTS

| | | |
|---|---|---|
| 5,860,990 A | 1/1999 | Nobles et al. |
| 5,997,552 A | 12/1999 | Person et al. |
| 6,071,292 A | 6/2000 | Makower |
| 6,152,935 A * | 11/2000 | Kammerer et al. ......... 606/144 |
| 6,206,895 B1 | 3/2001 | Levinson |
| 6,245,080 B1 | 6/2001 | Levinson |
| 6,319,263 B1 | 11/2001 | Levinson |
| 6,398,796 B2 | 6/2002 | Levinson |
| 6,425,900 B1 | 7/2002 | Knodel et al. |
| 6,491,707 B2 | 12/2002 | Makower et al. |
| 2001/0010005 A1 | 7/2001 | Kammerer et al. |
| 2001/0044638 A1 | 11/2001 | Levinson et al. |
| 2001/0044639 A1 | 11/2001 | Levinson |
| 2002/0087170 A1 | 7/2002 | Kuhns et al. |

* cited by examiner

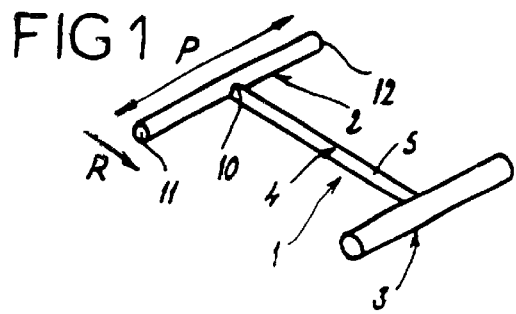
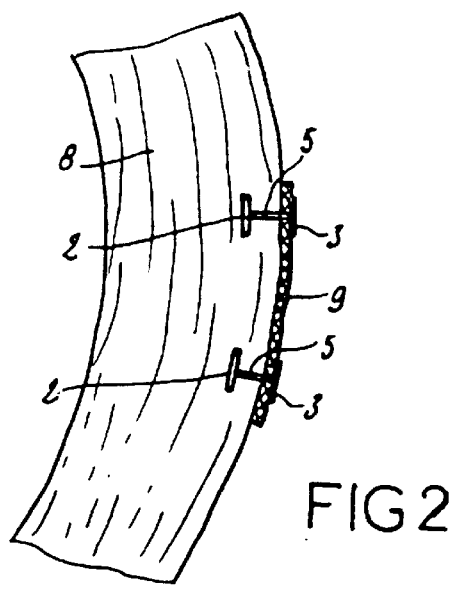
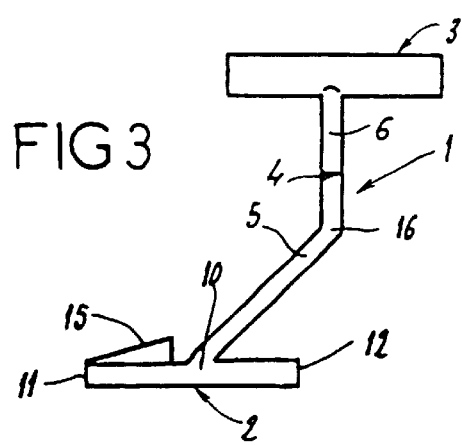
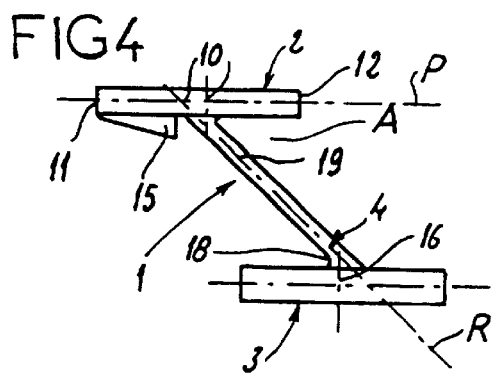
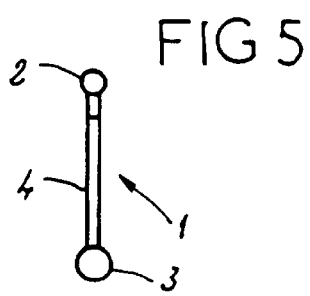
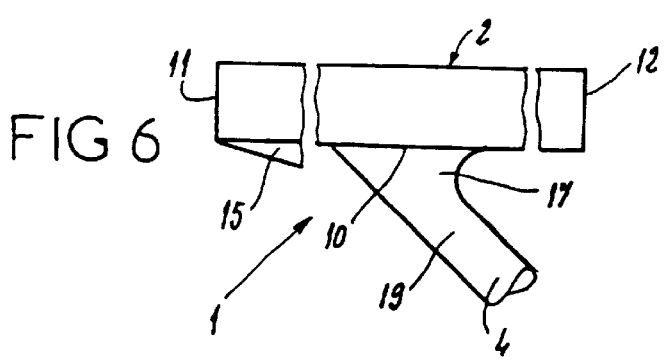

ABSORBABLE PROSTHETIC MOUNTING CLIP

The present invention relates to a prosthetic mounting clip made of biologically absorbable material, used for mounting a prosthetic part in the human body relative to an anatomical support.

According to the present invention, the terms used below in the description and in the claims have the following meanings:

"biologically absorbable material" is to be understood as meaning a material which is broken down and/or assimilated by and/or in the human or animal body;

"anatomical support" is to be understood as meaning nonmineralized human or animal support tissues.

In accordance with FIG. 17 of the document U.S. Pat. No. 5,203,864, a prosthetic mounting clip has been described and proposed in general, having a monolithic structure, made of a biologically absorbable material, comprising:

a distal element or anchoring rod in the anatomical support;

a proximal element or stop bar relative to a prosthetic part;

and a one-piece connecting rod, or strut, linking, on the one hand, the distal anchoring rod, at an intermediate point of the latter, and, on the other hand, the proximal stop bar, at an intermediate point of the latter.

The connecting rod is arranged relative to the distal anchoring rod so as to determine at least two relative or angular positions of said connecting rod, relative to the distal anchoring element, namely:

an inoperative position, corresponding to the initial position (that is to say after producing the clip, for example by molding or injection) of the connecting rod, in which the latter is arranged along a first direction, corresponding to the direction in which the clip is retained, by traction, in the anatomical support;

and a stressed position, with or without elastic return depending on the nature of the biologically absorbable plastic material, in which the connecting rod is folded back along a second direction, against the distal anchoring rod; this second direction corresponds to the direction in which the distal anchoring rod, folded back against the connecting rod, penetrates into and spaces apart the anatomical support in order to anchor the clip in the latter.

Such a clip can be placed in the anatomical support using any device in accordance with that described in the document U.S. Pat. No. 5,203,864 (cf. FIG. 14). This device includes in general a trocar in which a longitudinal continuous slot is formed, cooperating with an internal pusher. The distal anchoring rod of the clip is arranged in the trocar, with the connecting rod passing through the slot. By applying the distal end of the trocar from the outside against the anatomical support and by pushing the internal pusher against the anchoring rod, the latter and the folded-back connecting rod are made to penetrate into the orifice formed by the trocar. Then, when the distal anchoring rod has penetrated into the anatomical support, the trocar is withdrawn.

In accordance with the previously identified prior art, in the inoperative position of the connecting rod (made in one piece), the first direction of the latter is perpendicular to the second direction, also parallel to or coincident with the main direction or plane of the anchoring rod.

Such an arrangement has the disadvantage of applying, at the junction between the connecting rod and the distal anchoring rod, a considerable cumulative angular stress, since equal to 90°, in order to change from the inoperative position to the folded-back position of the connecting rod, plus 90°, when the clip is anchored in the anatomical support, in order to return to the inoperative position, under the effect of a traction applied from the proximal stop bar, that is to say 180° in total.

As the clip is made of a biologically absorbable plastic material, having mediocre elastic properties, this stress weakens the clip at the abovementioned junction, which often leads to its breaking between the connecting rod and the distal anchoring rod.

The object of the present invention is therefore to remedy this disadvantage. More precisely, the subject of the invention is an arrangement of the clip which limits the cumulative angular stress of the latter at the junction between the connecting rod and the distal anchoring rod.

According to the present invention, in the inoperative position of the connecting rod, at least part of the latter is inclined or oblique relative to the proximal stop bar and to the distal anchoring rod.

By virtue of the invention, for the aforementioned part of the connecting rod, the cumulative angular stress, calculated as before, is at most equal to 135°, in the case of a 45° inclination and a traction completely straightening the connecting rod, perpendicular to the distal anchoring rod.

This solution also brings with it other unexpected advantages.

When the aforementioned part of the connecting rod is straightened, that is to say arranged perpendicular to the distal anchoring rod, its original inclination makes it possible to provide extra anchoring depth, compared to the distance separating the distal anchoring rod and the proximal stop bar, for example parallel to one another. This permits more effective mounting of the clip in the anatomical support.

Nonetheless, the size of the clip in terms of width and height, that is to say the distance separating the anchoring rod and the stop bar, remains limited and remains compatible with the cross section of the tubular conduits used in surgery, in particular in celioscopy or laparoscopy, through which the clip is engaged in the anatomical support. In other words, for the same anchoring depth, the width or height taken up by a clip according to the invention is much less.

According to a preferred embodiment of the invention, a gusset is formed at the junction of the connecting rod with the distal anchoring rod, so that the zone of folding or axis of articulation of the connecting rod against the distal anchoring rod is shifted along the connecting rod, away from the junction zone between the distal anchoring rod and the connecting rod.

This makes it possible to distribute the mechanical bending, extension and traction stresses of the connecting rod relative to the distal anchoring rod about a greater radius of curvature, which fact limits the weakening of the biologically absorbable material at the junction between connecting rod and anchoring rod.

This gusset moreover limits the complete folding-back of the connecting rod on the distal anchoring rod and creates a sufficient interstice between the connecting rod and anchoring rod to promote fastening of the anchoring rod in the anatomical support as soon as the first traction stress arises, and thus promote the return to the inoperative position, and even beyond this if the traction continues.

According to another preferred characteristic of the present invention, the distal anchoring rod includes, at its own distal end, in the direction and in the sense of penetration into the anatomical support, at least one harpoon or redan in the form of a projection, permitting said anatomical support to be spaced apart. This projection, moving away from the distal anchoring rod, extends away from the proximal end of the distal anchoring rod in the direction toward the proximal end of the same rod.

Upon insertion of the clip into the anatomical support, this harpoon or redan makes it possible to transfer the zone of bending stress of the connecting rod from the proximal end of the clip away from the junction between the distal anchoring rod and the connecting rod. The advantage of this is that it causes minimal stressing of this junction zone, which is relatively weak, as has previously been stated.

Preferably in cooperation with the previously described gusset, the zone of bending stress which is situated toward the proximal and rear edge of the harpoon or redan corresponds precisely to the zone or axis of folding back of the connecting rod against the distal anchoring rod.

As regards the biologically absorbable material, the latter is preferably chosen from the group consisting of polymers of p-dioxanone, polyglycolides, polyorthoesters, polymers of trimethylene carbonate, stereocopolymers of L and D lactic acid, homopolymers of L lactic acid, copolymers of lactic acid and a compatible comonomer, such as the alpha-hydroxy acid derivatives. Still more preferably, the biologically absorbable material has a polydispersity of less than 2.

The invention will be better understood from the following description, with reference to the attached drawing in which:

FIG. 1 shows a perspective view of a mounting clip made of biologically absorbable material, according to the prior art;

FIG. 2 shows a transverse section through the mounting clip in FIG. 1, holding a prosthetic part against an anatomical support, such as a muscle wall;

FIG. 3 shows a plan view of a first embodiment of the biologically absorbable clip according to the invention;

FIGS. 4, 5 and 6 concern a second embodiment of a clip according to the invention; FIG. 4 is a plan view, on an enlarged scale, FIG. 5 is a side view, and FIG. 6 represents a detail from FIG. 4.

Referring to FIGS. 1 and 2, a prosthetic mounting clip 1 according to the prior art is represented. This clip 1 has a monolithic structure, which can be obtained, for example, by injection-molding of a biologically absorbable material, for example based for the most part on L lactic acid polymer, with a polydispersity of less than 2. The clip 1 includes a distal anchoring rod 2 and a proximal stop bar 3 which are linked via a connecting rod 4. The distal anchoring rod 2 and the proximal stop bar 3 are preferably and as represented in FIG. 1, and respectively extend transversely with respect to the connecting rod 4. The rod 2 and the bar 3 extend on either side of the connecting rod 4 in such a way as to form an "H".

The anchoring rod 2 extends in a first direction P of penetration and spacing-apart of an anatomical support 8, in which direction said rod is introduced as described previously. The connecting rod 4 extends in a second direction R of retention in which the clip 1 is retained in the anatomical support 8, by traction from the proximal stop bar 6. The connecting rod 4 is arranged relative to the anchoring rod 2 so as to have an inoperative position in which the connecting rod 4 is arranged along the direction of retention R, and a stressed position of penetration, folded back against the anchoring rod 2, in which the connecting rod 4 is arranged parallel to the direction of penetration P. As has been described above with reference to the patent U.S. Pat. No. 5,203,864, when the connecting rod 4 is folded back against the anchoring rod 2, the clip is then introduced through the prosthetic part 9 and into the anatomical support 8, via the distal end 11 of the anchoring rod 2, by a push on the proximal end 12 of this same rod 2. When the anchoring rod 2 has completely penetrated into the support, for example a muscle wall, the angulation at the junction 10 between the anchoring rod 2 and the connecting rod 4 acts, at the first traction on the clip, in such a way as to bring the connecting rod 4 back perpendicular to the anchoring rod 2, in its inoperative position. The clip thus finds itself retained between two planes of muscle fibers. At the same time, the proximal stop bar 3 arrests the penetrative displacement of the anchoring rod 7, by coming into abutment against the prosthetic part 9.

FIG. 3 shows a first embodiment of the clip according to the present invention. The same reference numbers have been used to designate the same elements as in FIGS. 1 and 2, and only the differences from these will be discussed.

The anchoring rod 2 in the first place includes a spacing projection 15 acting, as has already been stated, as a harpoon or redan extending away from the distal end 11 in the direction toward the proximal end 12. This spacing projection 15 has a surface inclined toward the proximal part of the clip. The inclination of a surface of the projection 15 makes it possible to ensure the spacing apart of the anatomical support, and also to displace the bending stress, exerted by the prosthetic tissue 9 and the muscle wall 8 on the connecting rod 4, further in the direction of the proximal stop bar 3, that is to say higher up on the connecting rod 4, as is represented in FIG. 3. The elevation of the bending stress point, caused by the projection, allows the connecting rod 4 to align itself in a substantially parallel manner to the direction of penetration P, without excessively stressing the junction between the anchoring rod 2 and the connecting rod 4.

Still referring to FIG. 3, the connecting rod 4 is inclined in a part 5 relative to the direction of penetration P of the anchoring rod 2, and for example at 45°. Moreover, the connecting rod 4 has a bend 16 and extends in another part 6 from the latter toward the stop bar 3, by forming a substantially right angle therewith, in such a way that the stop bar 3 remains substantially parallel to the anchoring rod 2.

In accordance with FIGS. 4 through 6, and according to a second embodiment of the invention, the prosthetic mounting clip 1 has, as before, a monolithic structure, made of a biologically absorbable plastic material, and comprises a distal anchoring rod 2 in the anatomical support 8, a proximal stop bar 3 relative to the prosthetic part 9, and a connecting rod 4 made in one piece linking the distal anchoring rod 2 and the proximal stop bar 3. Still as before, the connecting rod 4 is arranged relative to the distal anchoring rod 2 so as to determine at least two positions of this connecting rod 4, namely:

an inoperative position in which the connecting rod 4 is arranged along a first direction R;

and a stressed position in which the connecting rod 4 is folded back along a second direction P, corresponding to the direction of penetration into the anatomical support 8 of the distal anchoring rod 2, and this against the latter.

According to the invention, in the inoperative position of the connecting rod 4, the first direction R is inclined relative to the second direction P, parallel or identical to that of the anchoring rod 2, and this at an angle for example equal to about 45°.

The connecting rod 4 joins the distal anchoring rod 2 at an intermediate point 10 of the latter, for example at the center.

As has been described with reference to FIG. 3, the distal anchoring rod 2 includes at least one spacing projection 15, having the form of a redan or harpoon, provided in the direction P, extending away from the distal end 11 in the direction toward the proximal end 12 of the distal anchoring rod 2.

The connecting rod 4 joins the proximal stop bar 3 at an intermediate point 16 of the latter, for example at the center.

The proximal bar 3 has a larger cross section than that of the distal anchoring rod 2. And the connecting rod 4 has an intermediate cross section between those of the proximal stop bar 3 and of the distal anchoring element 2, respectively.

In the inoperative position of the connecting rod 4, corresponding to the configuration of the clip before its use, this connecting rod, the proximal stop bar 3 and the distal anchoring rod 2 are arranged substantially in the same plane. The stop bar 3 and the anchoring rod 2 are arranged substantially parallel to one another, with the connecting rod 4 in an inclined or oblique position relative to the stop bar 3 and to the anchoring rod 2.

As can best be seen in FIG. 6, a gusset 17 is formed at the junction of the connecting rod 4 with the distal anchoring rod 2, so that the zone 19 of folding or axis of articulation of the connecting rod 4 to come against the distal anchoring rod 2 is shifted along this rod 4, away from the junction zone 10 between the distal anchoring rod 2 and the connecting rod 4.

A gusset 18 of the same type is formed on the side opposite the gusset 17, at the junction of the connecting rod 4 with the proximal stop bar 3.

EXAMPLE

A clip according to the embodiment in FIGS. 4 through 6 has been produced using a biologically absorbable material, comprising an L lactic acid polymer, manufactured and sold by the company PHUSIS under the name PHUSILINE® PLA 98, and with the following dimensions:

the anchoring rod 2 has a cross section of diameter 0.9 mm, with a length of 7 mm;

the stop bar 3 has a cross section of diameter 1.2 mm, with a length of 7.2 mm;

the connecting rod 4 has a cross section of diameter 0.55 mm, and it is inclined at 45° relative to the rod 2 and to the bar 3;

the distance separating the axes of the bar 3 and of the rod 2 is equal to 6.5 mm.

This clip is tested by comparison with a control clip, made of traditional plastic material, namely polypropylene, retaining substantially the same dimensions and the same shape.

These clips are tested on the quadriceps and the patellar tendon of a lamb, namely on the outer surface of the thigh (conventional muscle tissue with aponeurosis covering), and on the patellar tendon (dense fibrous tissue of low thickness covering a cavity)

Traction tests are carried out using a tensiometer to measure the force needed to pull out the clip.

The following table summarizes the tearing-out forces in N.

| | | | |
|---|---|---|---|
| Clip according to the invention | Outer thigh | 13.19 | Standard deviation 3.46 |
| | Tendon | 14.95 | Standard deviation 2.56 |
| Control clip, in polypropylene | Outer thigh | 14.11 | Standard deviation 2.33 |
| | Tendon | 14.68 | Standard deviation 3.23 |

By virtue of the invention, and notwithstanding the limited mechanical properties of the biologically absorbable material, a pulling-out force is obtained which is of the same order as that obtained with a traditional plastic material. Furthermore, this force is of the same order as that obtained, under the same conditions, with metal clips, for example having values of the order of 13 N.

What is claimed is:

1. Prosthetic mounting clip, having a monolithic structure, made of a biologically absorbable plastic material, comprising a distal anchoring rod capable of being anchored in an anatomical support, a proximal stop bar relative to a prosthetic part, and a connecting rod connected to and extending between an intermediate connection point of the distal anchoring rod and an intermediate connection point of the proximal stop bar, the connecting rod having no more than one bend to define no more than two rod portions, the connecting rod being arranged relative to the distal anchoring rod so as to determine at least two positions of said connecting rod, namely an inoperative position in which at least a part of the connecting rod is arranged along a first direction relative to the distal anchoring rod, and a stressed position in which said part of the connecting rod is folded back against the distal anchoring rod along a second direction, and, in the inoperative position of the connecting rod, the proximal stop bar and the distal anchoring rod are arranged substantially in the same plane, said stop bar and said distal anchoring rod being arranged substantially parallel to one another and not along a same line, wherein, in the inoperative position of the connecting rod, at least the part of the connecting rod is in an inclined or oblique position relative to said proximal stop bar and to said distal anchoring rod at the connection points.

2. Clip according to claim 1, wherein, in the inoperative position of the connecting rod, the first direction is inclined relative to the second direction at an acute angle of less than or equal to 90°, the second direction being parallel to the distal anchoring rod.

3. Clip according to claim 2, wherein the acute angle is equal to about 45°.

4. Prosthetic mounting clip, having a monolithic structure, made of a biologically absorbable plastic material, comprising a distal anchoring rod capable of being anchored in an anatomical support, a proximal stop bar relative to a prosthetic part, and a connecting rod connected to and extending between an intermediate point of the distal anchoring rod and an intermediate point of the proximal stop bar, the connecting rod being arranged relative to the distal anchoring rod so as to determine at least two positions of said connecting rod, namely an inoperative position in which at least a part of the connecting rod is arranged along a first direction relative to the distal anchoring rod, and a stressed position in which said part of the connecting rod is folded back against the distal anchoring rod along a second direction, and, in the inoperative position of the connecting rod, the proximal stop bar and the distal anchoring rod are arranged substantially in the same plane, said stop bar and said distal anchoring rod being arranged substantially parallel to one another, wherein, in the inoperative position of the connecting rod, at least the part of the connecting rod is in an inclined or oblique position relative to said proximal stop bar and to said distal anchoring rod, wherein the distal anchoring rod includes at least one spacing projection provided in the second direction, extending from a first end in a direction toward a second end of the distal anchoring rod, the first end of the distal anchoring rod being farther from the proximal stop bar when the connecting rod is in the inoperative position.

5. Prosthetic mounting clip, having a monolithic structure, made of a biologically absorbable plastic material, comprising a distal anchoring rod capable of being anchored in an anatomical support, a proximal stop bar relative to a prosthetic part, and a connecting rod connected to and extending between an intermediate point of the distal anchoring rod and an intermediate point of the proximal stop bar, the connecting rod being arranged relative to the distal anchoring rod so as to determine at least two positions of said connecting rod, namely an inoperative position in which at least a part of the connecting rod is arranged along a first direction relative to the distal anchoring rod, and a stressed position in which said part of the connecting rod is folded back against the distal anchoring rod along a second direction, and, in the inoperative position of the connecting rod, the proximal stop bar and the distal anchoring rod are arranged substantially in the same plane, said stop bar and said distal anchoring rod being arranged substantially parallel to one another, wherein, in the inoperative position of the connecting rod, at least the part of the connecting rod is in an inclined or oblique position relative to said proximal stop bar and to said distal anchoring rod, wherein the proximal stop bar has a greater cross section than that of the distal anchoring rod.

6. Clip according to claim 5, wherein the connecting rod has an intermediate cross section between those of the proximal stop bar and of the distal anchoring rod, respectively.

7. Prosthetic mounting clip, having a monolithic structure, made of a biologically absorbable plastic material, comprising a distal anchoring rod capable of being anchored in an anatomical support, a proximal stop bar relative to a prosthetic part, and a connecting rod connected to and extending between an intermediate point of the distal anchoring rod and an intermediate point of the proximal stop bar, the connecting rod being arranged relative to the distal anchoring rod so as to determine at least two positions of said connecting rod, namely an inoperative position in which at least a part of the connecting rod is arranged along a first direction relative to the distal anchoring rod, and a stressed position in which said part of the connecting rod is folded back against the distal anchoring rod along a second direction, and, in the inoperative position of the connecting rod, the proximal stop bar and the distal anchoring rod are arranged substantially in the same plane, said stop bar and said distal anchoring rod being arranged substantially parallel to one another, wherein, in the inoperative position of the connecting rod, at least the part of the connecting rod is in an inclined or oblique position relative to said proximal stop bar and to said distal anchoring rod, wherein a gusset is formed at a junction of the connecting rod with the distal anchoring rod, such that a zone of folding of the connecting rod against the distal anchoring rod is located along the connecting rod, away from the junction of the distal anchoring rod and the connecting rod.

* * * * *